US012751682B2

(12) United States Patent
Ostmeier et al.

(10) Patent No.: US 12,751,682 B2
(45) Date of Patent: Oct. 6, 2026

(54) RANDOM SAMPLING FOR DEEP LEARNING SEGMENTATION OF ACUTE ISCHEMIC STROKE ON NON-CONTRAST CT

(71) Applicant: The Board of Trustees of the Leland Stanford Junior University, Stanford, CA (US)

(72) Inventors: Anna Sophie Gertrud Ostmeier, Portola Valley, CA (US); Brian M. Axelrod, Portola Valley, CA (US); Jeremy J. Heit, Redwood Cit, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

(21) Appl. No.: 18/435,192

(22) Filed: Feb. 7, 2024

(65) Prior Publication Data

US 2025/0275735 A1 Sep. 4, 2025

Related U.S. Application Data

(60) Provisional application No. 63/443,809, filed on Feb. 7, 2023.

(51) Int. Cl.
*A61B 6/50* (2024.01)
*A61B 6/03* (2006.01)
(Continued)

(52) U.S. Cl.
CPC .............. *A61B 6/501* (2013.01); *A61B 6/032* (2013.01); *G06T 7/10* (2017.01); *G16H 30/20* (2018.01);
(Continued)

(58) Field of Classification Search
CPC ........... A61B 6/501; A61B 6/032; G06T 7/10; G06T 2207/20084; G06T 2207/10081;
(Continued)

(56) References Cited

U.S. PATENT DOCUMENTS

| | | | | |
|---|---|---|---|---|
| 11,625,832 B2 * | 4/2023 | Mansi | ..................... | G16H 50/20 382/128 |
| 2021/0093258 A1 * | 4/2021 | Kalafut | .................. | A61B 6/032 |

OTHER PUBLICATIONS

Kuang, H., et al. "Automated ASPECTS on Non contrast CT scans in patients with acute ischemic stroke using machine learning." American journal of neuroradiology 40.1 (2019): 33-38. (Year: 2019).*

(Continued)

*Primary Examiner* — Matthew C Bella
(74) *Attorney, Agent, or Firm* — LUMEN PATENT FIRM

(57) ABSTRACT

A method is described for generating segmentation masks to assist in identification of acute ischemic stroke. The method includes performing by a non-contrast computed tomography scan to produce a computed tomography image; inputting the computed tomography image to an input layer of a deep learning neural network; and outputting a segmentation mask of acute ischemic stroke from an output layer of the deep learning neural network, wherein the segmentation mask of acute ischemic stroke is generated in response to the computed tomography image input to the deep learning neural network. The deep learning neural network is trained with ground truth non-contrast computed tomography images and corresponding segmentation masks of acute ischemic stroke, wherein multiple segmentation masks of acute ischemic stroke for each of the non-contrast computed tomography images are randomly sampled for training.

5 Claims, 13 Drawing Sheets

(51) Int. Cl.
*G06T 7/10* (2017.01)
*G16H 30/20* (2018.01)
*G16H 30/40* (2018.01)

(52) U.S. Cl.
CPC ........................ *G16H 30/40* (2018.01); *G06T 2207/20084* (2013.01)

(58) Field of Classification Search
CPC ........... G06T 2207/20081; G06T 2207/30016; G06T 2207/30101; G06T 7/11; G16H 30/20; G16H 30/40; G16H 50/20
See application file for complete search history.

(56) References Cited

OTHER PUBLICATIONS

Kuang, Hulin, et al. “EIS-Net: Segmenting early infarct and scoring ASPECTS simultaneously on non-contrast CT of patients with acute ischemic stroke.” Medical Image Analysis 70 (2021): 101984. (Year: 2021).*
Kuang, Hulin, Bijoy K. Menon, and Wu Qiu. “Segmenting hemorrhagic and ischemic infarct simultaneously from follow-up non-contrast CT images in patients with acute ischemic stroke.” IEEE Access 7 (2019): 39842-39851. (Year: 2019).*
Wang, Chengyan, et al. “Deep learning-based identification of acute ischemic core and deficit from non-contrast CT and CTA.” Journal of Cerebral Blood Flow & Metabolism 41.11 (2021): 3028-3038. (Year: 2021).*
Cao, Zehong, et al. Deep learning derived automated ASPECTS on non-contrast CT scans of acute ischemic stroke patients. vol. 43. No. 10. Hoboken, USA: John Wiley & Sons, Inc., 2022. (Year: 2022).*
Ostmeier et al., USE-Evaluator: Performance Metrics for Medical Image Segmentation Models with Uncertain, Small or Empty Reference Annotations. Nov. 1, 2022, arXiv:2209.13008v3 [eess.IV].
Lemay et al., Label fusion and training methods for reliable representation of inter-rater uncertainty. Feb. 26, 2022. arXiv:2202.07550v2 [eess.IV].
Ostmeier et al., Random Expert Sampling for Deep Learning Segmentation of Acute Ischemic Stroke on Non-contrast CT, Sep. 7, 2023, arXiv:2309.03930 [cs.CV].
Kohl et al. “A probabilistic u-net for segmentation of ambiguous images,” Advances in neural information processing systems, vol. 31, 2018. arXiv:1806.05034 [cs.CV].

* cited by examiner

RANDOM SAMPLING FOR DEEP LEARNING SEGMENTATION OF ACUTE ISCHEMIC STROKE ON NON-CONTRAST CT

CROSS-REFERENCE TO RELATED APPLICATIONS

This application claims priority from U.S. Provisional Patent Application 63/443,809 filed Feb. 7, 2023, which is incorporated herein by reference.

FIELD OF THE INVENTION

The invention relates generally to computed tomography (CT). More specifically, it relates to techniques for segmentation of CT images to aid in the identification of acute ischemic stroke.

BACKGROUND OF THE INVENTION

Stroke is a leading cause of death and disability globally. Timely treatments, such as thrombolysis or thrombectomy, represent effective treatment options to improve clinical outcomes for patients suffering from acute ischemic stroke. Non-Contrast CT (NCCT) is widely used to differentiate ischemic from hemorrhagic stroke, and it is performed on nearly all patients who present with acute ischemic stroke. NCCT can be further used to estimate the extent of irreversibly damaged brain tissue as an imaging biomarker for the appropriate triage of patients.

The Alberta Stroke Program Early CT Score (ASPECTS) is an established semi-quantitative method to evaluate treatment eligibility in ischemic stroke patients based on NCCT by dividing the affected hemisphere into 10 structural regions. However, the extent and relative quantity of damaged brain tissue within a region to be rendered has been defined vaguely and ASPECTS suffers from relatively poor inter-rater agreement. A tool that accurately localizes and quantifies infarcted brain tissue on NCCT would be highly desirable to better guide treatment decisions and patient prognostication. However, a low contrast-to-noise ratio between normal and infarcted brain tissue leads to high interobserver variability for expert neuroradiologists and limits rule-based algorithms to segment ischemic stroke on NCCT. An automated artificial intelligence pipeline is therefore of high interest.

Supervised deep learning models have been widely applied for the segmentation of medical images. Although they show promise for applications in stroke imaging, they rely on accurate reference annotations segmentation during training. However, a low signal-to-noise ratio restricts rule-based algorithms and expert neuroradiologists for the segmentation of ischemic stroke on NCCT. This difficulty results in uncertainty (inter-expert disagreement) of the experts reference annotation.

Prior works focus on returning calibrated uncertainty estimates to inform clinicians about the model confidence of its prediction, and model uncertainty. Kohl et al. ("A probabilistic u-net for segmentation of ambiguous images," Advances in neural information processing systems, vol. 31, 2018) propose the probabilistic U-Net to encode inter-rater uncertainty and to provide clinicians distributions over possible segmentations rather than point estimates. However, providing multiple possible segmentations which need time and expertise to evaluate is of limited value because diagnosis using acute stroke imaging is highly time-sensitive. A model that directly predicts a probability heatmap or a binary segmentation seems more useful.

In a segmentation task with reference annotation of high uncertainty, small target lesions, or empty segmentations reference annotations require at least highly skilled experts to minimize the errors, and multiple experts segmentations are needed to approximate the distribution of interpretations. Because this is resource-intensive and timely, prior work used synthetic target lesions for ischemic stroke on NCCT or co-registered target lesions from MR imaging with positive results. These approaches may suffer from the dependency on co-registration quality, unclear imaging correlates between modalities and time from NCCT to MR imaging. More commonly, deep learning medical image segmentation are supervised by human experts annotations and fusion methods (e.g. majority vote) may approximate an error-free ground truth when collecting annotations from multiple experts. For acute ischemic stroke segmentation on NCCT, fusion methods for categorical voxel classes may limit the ability of the model to learn segmentation tasks where experts inherently disagree. One approach to enhance the accuracy of ground truth segmentation is the fusion of multiple expert annotations using a majority or probabilistic vote, such as the STAPLE algorithm. The result is a binary ground truth (a voxel is part of the ischemic core or not). However, STAPLE algorithm does not converge in instances where the labels greatly differ, i.e., if one or more experts do not identify any ischemic stroke lesion, which can frequently occur when segmenting hypodense tissue on NCCT. These advanced fusion methods, such as STAPLE or SIMPLE, are not applicable and majority voting only shows modest performance.

Thus, there remains a need for improved techniques for acute ischemic stroke segmentation on NCCT.

BRIEF SUMMARY OF THE INVENTION

Outlining acutely infarcted tissue on non-contrast CT is a challenging task for which human inter-reader agreement is limited. This work provides a method for using a deep learning algorithm to perform segmentation using a network trained randomly on separate individual expert segmentations. Specifically, a U-Net was trained to segment ischemic brain tissue using random expert sampling on the reference annotations of experienced neuroradiologists. This random expert sampling method model outperformed inter-expert agreement and a majority model. In addition, the random-model predicted volume correlated to the clinical outcome, whereas the median expert volume and majority-model volume did not.

In contrast to prior studies which have trained and fine-tuned models on single expert segmentations to outline ischemic stroke on NCCT, this multi-expert training technique improves performance beyond the expert level. This provides an automated and reliable tool for ischemic stroke analysis.

Herein is described a deep learning network prediction and training technique that uses interpretations of multiple expert neuroradiologists for training and predicts acute ischemic stroke segmentations that agree with the experts better than the experts agree with themselves.

A segmentation methodology superior to experts allows more on-call clinicians to utilize the information given by NCCT for the clinical decision tree.

In clinical practice, our method can more reliably identify, quantify, and localize acute ischemic stroke on NCCT compared to experts. This possibly enhances the impact of NCCT in endovascular treatment decisions for ischemic strokes as a basic, cheap, and widely available imaging modality.

This technique can provide automatic segmentation of acute ischemic stroke in NCCT to assist in triaging patients for optimal treatment.

This can save additional imaging and time from symptom onset to treatment, which is highly correlated to the clinical outcome. Current imaging modalities that are used for this purpose involve more involved imaging procedures, round-the-clock expert availability, specialized technicians, additional contrast agent, and radiation exposure. Therefore, it is only available in specialized hospitals, whereas NCCT is available in almost every hospital.

In one aspect, the invention provides a method for generating segmentation masks to assist in identification of acute ischemic stroke, the method comprising: performing by a non-contrast computed tomography scan to produce a computed tomography image; inputting the computed tomography image to an input layer of a deep learning neural network; and outputting a segmentation mask of acute ischemic stroke from an output layer of the deep learning neural network, wherein the segmentation mask of acute ischemic stroke is generated in response to the computed tomography image input to the deep learning neural network; wherein the deep learning neural network is trained with ground truth non-contrast computed tomography images and corresponding segmentation masks of acute ischemic stroke, wherein multiple segmentation masks of acute ischemic stroke for each of the non-contrast computed tomography images are randomly sampled for training. The method is not restricted to randomly sampling different manual ground truth labels of neuroradiologists, but may alternatively use random sampling ground truth labels that are derived from different imaging modalities if in close time proximity to the NCCT. Preferably, the deep learning neural network has a nnUNet architecture with multiple stages with two 3D convolutions per stage, and leaky ReLU as activation function.

DETAILED DESCRIPTION OF THE INVENTION

Figure 1:
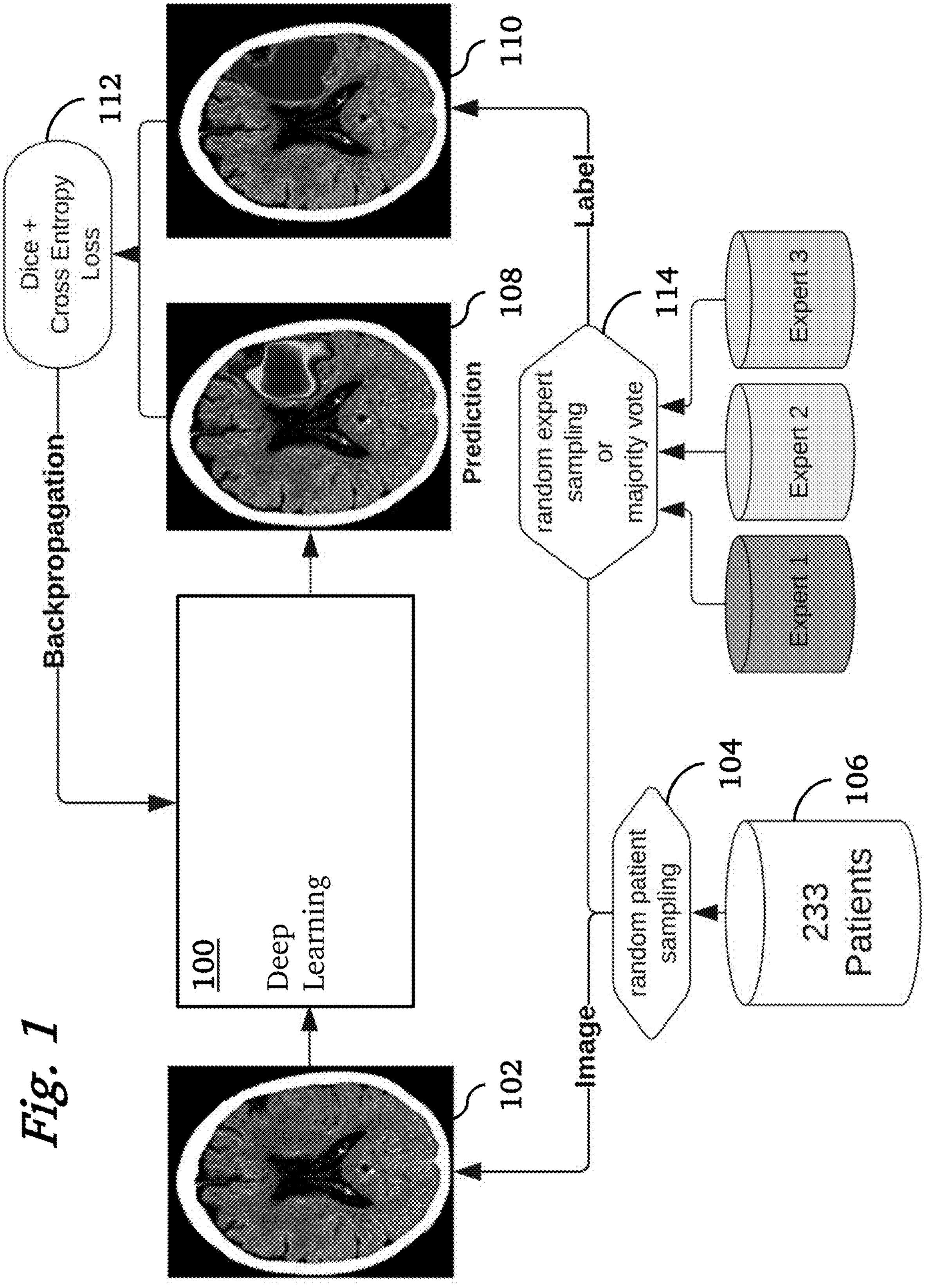
FIG. 1 is a schematic training scheme processing pipeline with sampling strategy for random expert sampling and majority vote, according to an embodiment of the invention.

The present invention provides a new artificial intelligence model based on random expert sampling, such that an expert segmentation that defines the ground truth for each training example is randomly selected during training (random-model). To demonstrate the superiority of this technique and present its operation, we compare the random-model's performance first to the inter-expert agreement and secondly to the majority vote binarized ground truth approach (majority-model). The random-model leads to better performance than the inter-expert agreement and the majority-model for developing an automated algorithm to identify early ischemic signs on NCCT.

The random model of the present invention is compared with other approaches here using a post hoc analysis of the randomized DEFUSE 3 trial, in which 260 head NCCT examinations from 233 patients are included. The primary trial outcome determined thrombectomy eligibility for patients with acute ischemic stroke within 6-16 hours of symptom onset. Furthermore, 156 consecutive patients without an ischemic stroke from a database were included to evaluate an image classification task (lesion versus no lesion). These patients underwent an NCCT for symptoms that were consistent with an acute ischemic stroke from 2011 to 2017, but all were confirmed to have no cerebral infarction with a normal DWI scan 24 h after the initial NCCT. We also included NCCT from ischemic stroke patients (1723 patients) as an external generalization cohort. We randomly chose 35 of these patients, who underwent NCCT between 2016 through 2019. Each of these patients had a symptom onset time 3-24 hours before NCCT. We excluded 2 NCCT due to unacceptable quality.

In this analysis, three experienced fellowship-trained neuroradiologists (experts A, B, and C) with 6, 4, and 10 years of post-fellowship experience manually segmented acute infarcts in Horos (Horosproject.org, version 4.0.0). The experts were given the information that each patient had a large vessel occlusion, but the side of the vessel occlusion was not provided. If no abnormal hypodensity was found, experts were offered the option of no segmentation. All manual segmentations were checked for correct co-registration to the NCCT. For the data set of the stroke-negative patients, an empty segmentation mask was generated. To ensure the model's robustness in clinical settings, where data is more diverse and less regulated than in a clinical trial, our external test set differs on two fronts from the internal test set. First, it includes NCCT from unseen institutions and the general clinical population. Second, we use two fellowship-trained neuroradiologists both with 1 year of post-fellowship training to ensure that the relative performance comparison of the model holds up beyond our choice of expert raters.

Data Preparation for Training

Figure 5:
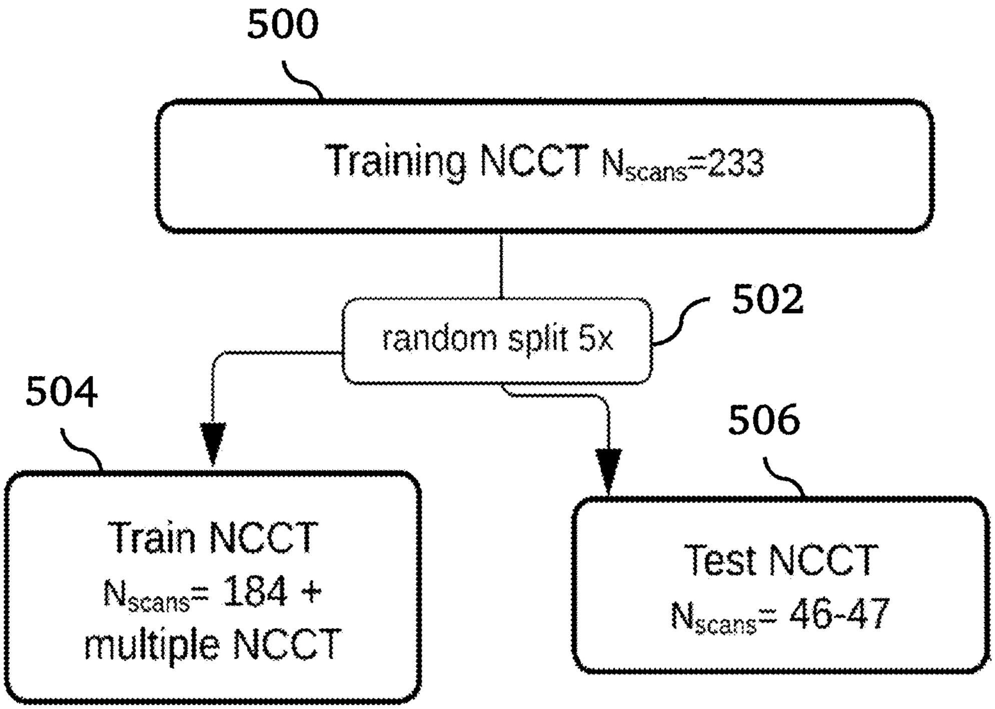
FIG. 5 is a flowchart illustrating a method for the data partition, according to an embodiment of the invention. 233 patients with their initial NCCT were randomly split into 5 folds of training and test sets. 25 patients had multiple NCCT. Those were only assign to the initial NCCT when in the training set. The external generalization cohort included 33 patients.

The cohort of 233 patients was randomly split into five subgroups for five-fold cross-validation with 208 patients for the training, and 25 for the test sets. If a patient had undergone multiple baseline NCCT (n=27 patients), the additional scans were only added to the corresponding patient NCCT in the training set to prevent information leakage. The 156 healthy cases were randomly and equally added to the test sets (n=33 per test set) with empty ground truth annotations. FIG. 5 is a flowchart illustrating the method for the data partition, according to an embodiment of the invention. 233 patients with their initial NCCT 500 were randomly split 502 into 5 folds of training sets 504 and test sets 506. 25 patients had multiple NCCT. Those were only assigned to the initial NCCT when in the training set. The external generalization cohort included 33 patients.

Model Configuration and Training

A preprocessing pipeline and data loader were created to allow on-the-fly majority vote and random expert sampling. FIG. 1 is a schematic training scheme processing pipeline with sampling strategy for random expert sampling and majority vote, according to an embodiment of the invention. A deep learning network 100 takes as input an image 102 and outputs a predicted image segmentation 108, i.e., labels associated with regions of the image. During training, the image 102 is produced by random patient sampling 104 from among the 233 patients 106. For the selected patient, random expert sampling 114 selects labels associated with a randomly-selected expert's segmentation labels 110 for that patient's image. Random expert sampling means choosing an expert for each training example uniformly. That means that every training example during training is expected to be paired with each of the experts' labels ⅓ of the times. The expert segmentation labels 110 are compared with the predicted segmentation labels 108 using Dice+cross-entropy loss 112 to train the network 100 using backpropagation. Once trained, the network 100 is used in a clinical setting to predict segmentation labels 108 from a clinical image 102 produced from a NCCT scan of a patient.

The network model 100 was trained with NCCT image 102 as input and manual annotation labels 110 of experts as ground truth to output a predicted segmentation mask 108 of acute ischemic stroke on NCCT. As all models share the same core nnUNet component and for fairness and ease of comparability of methods, we let all models undergo the same training schedule with default hyperparameters to prevent information leakage.

In the analysis that compares the random expert sampling with other techniques, instead of random expert sampling 114, majority vote can be used during training of the network 100. Majority vote means to sum the reference masks of all experts, set the voxels with a value greater than half the number of experts to one, and all other voxels to zero.

Figure 7:
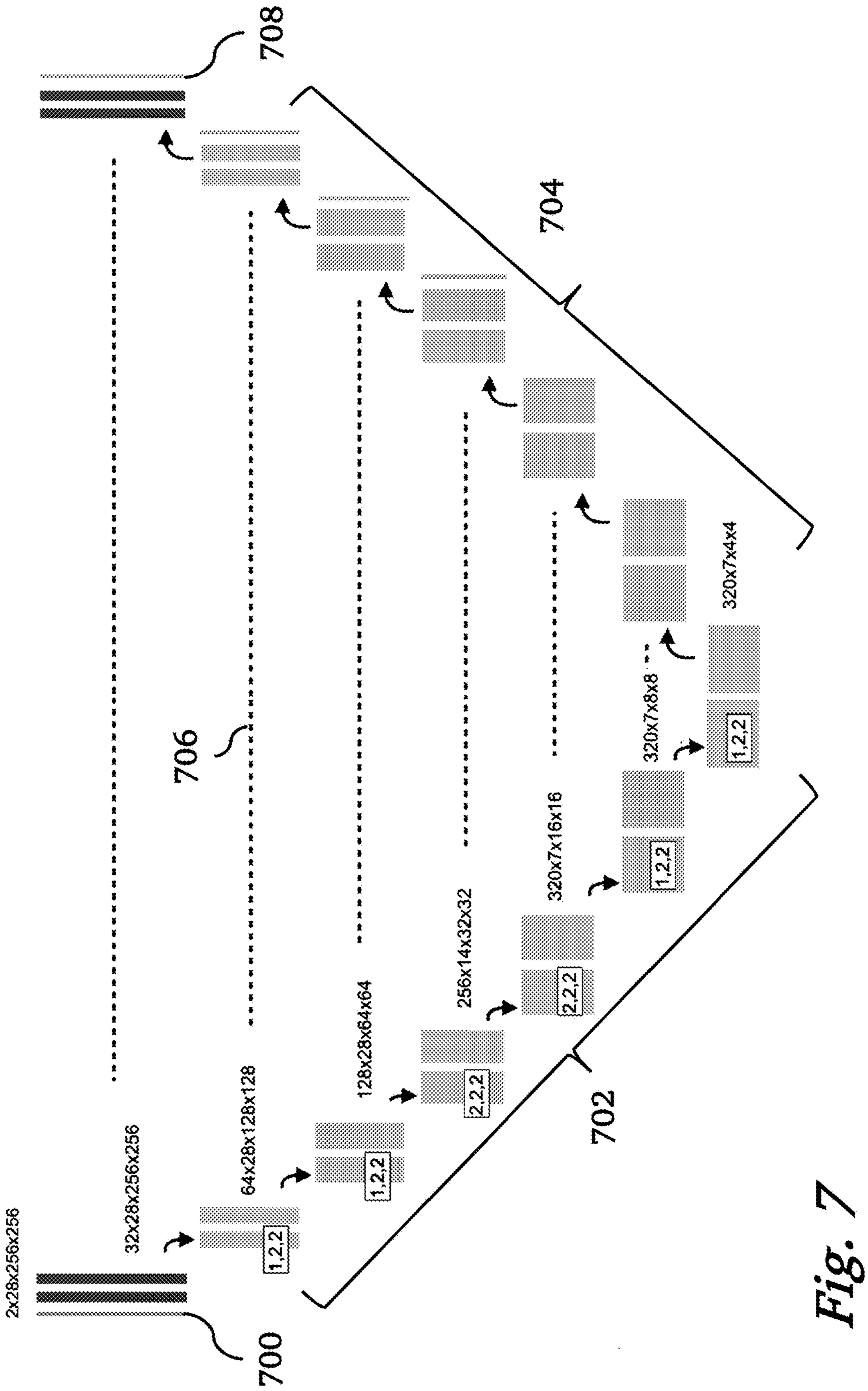
FIG. 7 is a schematic diagram of a convolutional neural network Model Architecture, according to an embodiment of the invention. The modified nnUNet configuration includes a large patch size of 28×256×256, 7 stages with two 3D convolutions per stage. The output of the model was a segmentation mask), a spacing of (3.00, 0.45, 0.45) and dimensions of 22-56×512×512. The parameter space after each stage is denoted in pytorch's tensor convention (channels×depth×height×width).

FIG. 7 is a schematic diagram illustrating the architecture of a convolutional neural network (100, FIG. 1) according to an embodiment of the invention. This modified nnUNet configuration includes a large patch size of 28×256×256 and spacing of (3.00, 0.45, 0.45), 7 stages with two 3D convolutions per stage, leaky ReLU as activation function, Soft Dice+Cross-Entropy loss function, a batch size of 2, SGD optimizer with 0.99 Nestov momentum and He initialization. The output of the model is a segmentation mask with a spacing of (3.00, 0.45, 0.45) and dimensions of 22-56×512×512. The parameter space after each stage is denoted in pytorch's tensor convention (channels×depth×height×width). The NCCT image is input to an input layer 700 of the network which is followed by two conv-IN-lReLU layers. The data progresses down through subsequently deeper encoder levels 702, each with a pair of conv-IN-lReLU layers, then progresses back up through decoder levels 704, each with a pair of conv-IN-lReLU layers. These encoder and decoder levels are connected at corresponding depths with skip connections 706. The highest three decoder levels include a conv-softmax layer. The top level includes two conv-IN-lReLU layers followed by a conv-softmax layer, which is the output layer 708. The network may be implemented using two NVIDIA Geforce RTX 3090 24 GB processors during training and inference.

We trained for a constant number of 700 epochs by which all models during cross-validation visually converged. FIGS. 9A-9E show training loss graphs for random expert sampling (random model) for five folds of training sets. The middle line in each graph is the test loss, the bottom line is the training loss, and the top line is the estimated dice performance. The left y-axis describes the loss, the right y-axis describes the estimated dice performance and the x-axis describes the number of epochs. All models converged by epoch 700.

Model Testing

All analyses were performed on the aggregated test sets of the five folds. The results of the aggregated test sets (n=233+156=389) were tested for normal distribution with the Shapiro test and shown as median and 95% CI estimated by the bootstrapping (R=1000). We tested random-model and majority vote on the external generalization cohort.

Outcome Measures and Statistical Analysis

Figure 6:
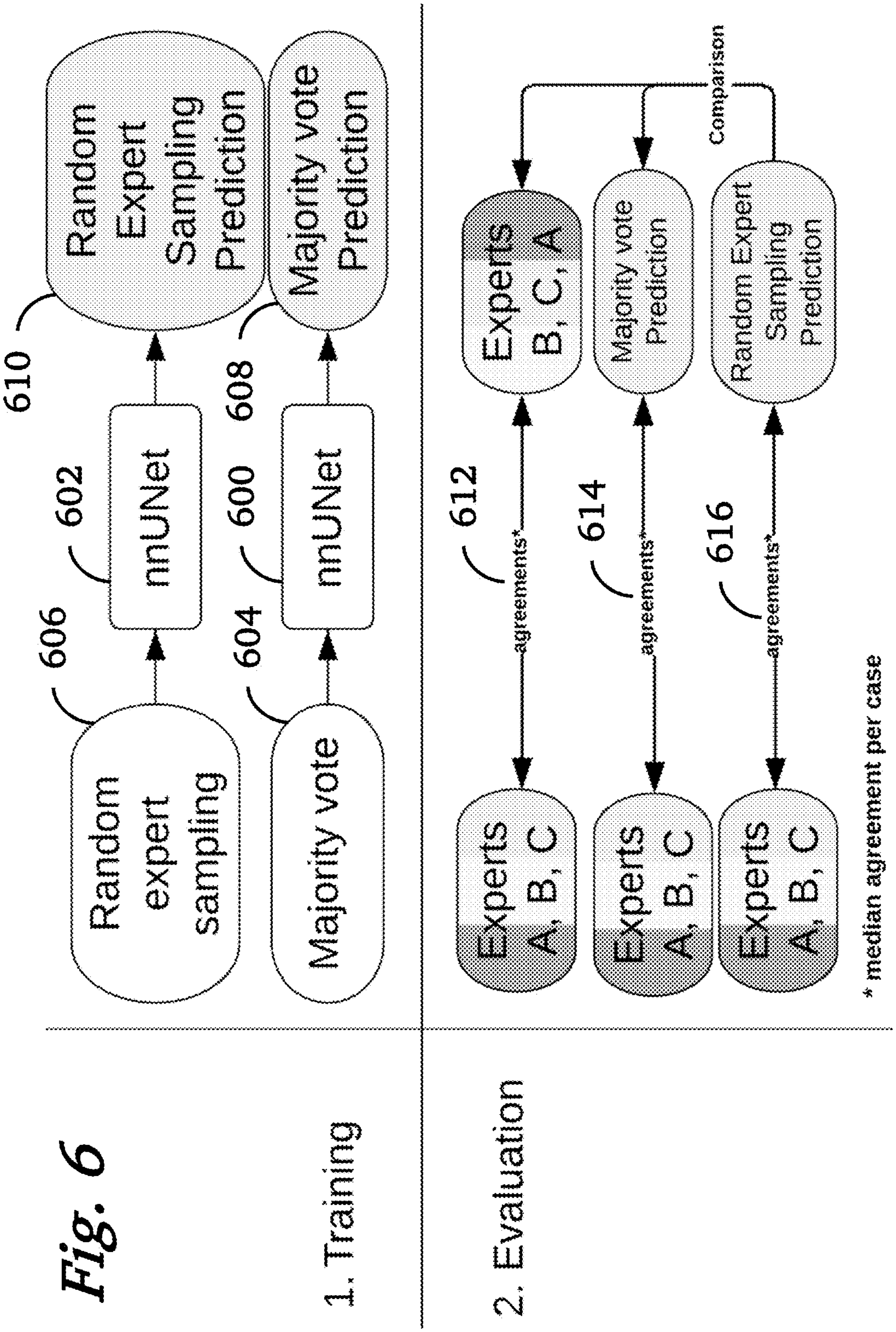
FIG. 6 is a schematic diagram illustrating training and evaluation steps, according to an embodiment of the invention. First, two models were trained on majority vote and random expert sampling. Second, the median agreement per case for inter-expert agreement, model-expert agreement for the prediction of the majority vote, and random expert sampling was the basis to compare random expert sampling to the majority vote and inter-expert agreement.

We determined each pair of inter-expert agreements for each NCCT (expert A and B, expert A and C, expert B and C) and then summarized as the three inter-expert agreements the median per NCCT. We then compared each expert to the prediction of the majority vote and the random-model (expert A and model, expert B and model, expert C and model). FIG. 6 is a schematic diagram illustrating training and evaluation steps, according to an embodiment of the invention. First, two models 600, 602 were trained on majority vote 604 and random expert sampling 606 to make predictions 608 and 610, respectively. Second, for evaluation, the median agreement per case for inter-expert agreement 612, model-expert agreement for the prediction of the majority vote 614, and random expert sampling 616 was the basis to compare random expert sampling to the majority vote and inter-expert agreement.

We again took the median per NCCT. We use the inter-expert agreement as a baseline and compare it to the model performance of the two training regimes. The model-based predictions were evaluated for segmentation accuracy, image classification (lesion versus no lesion), volume classification, correlation to CT ischemic core (<30% CBF), 24 h-follow-up volume, and clinical outcome prediction.

For the segmentation and image classification task, a clinically motivated threshold of 1 ml was chosen to differentiate between lesion and no lesion cases. For example, after determining no relevant stroke volume on the NCCT, the location, and volume of ischemic brain tissue of 1 ml is unlikely to influence the triage of patients and excluded from the segmentation evaluation. Experts A, B, and C had 78, 7, and 27 manual segmentations <1 ml, respectively. Experts D and E had 14 and 11 manual segmentations <1 ml, respectively.

All NCCTs with a median reference annotation above 1 ml were evaluated for segmentation error with the following metrics.

Volume-based metrics (Volumetric similarity and absolute volume difference [ml])

Overlap metrics (Dice, Precision and Recall).

Distance metrics Hausdorff distance with the 95 percentile [mm], and the surface dice at tolerance 5 mm The definition can be found in Table 5.

For the image classification task, the predictions were categorized in stroke volume above or below 1 ml including the non-stroke cases. Sensitivity, specificity, F-score, Correct Classification Ratio, and area under the curve served as metrics. For defining binary metrics, a threshold of 1 ml was applied to the output of the models.

We tested for statistical superiority with a two-sided Wilcoxon sign rank test (p<0.05, FIG. 3). All p-values were adjusted for multiple comparisons with the Holm-Bonferroni method. R (Version 2022.02.3) was used for statistical analysis. A p-value <0.05 represents a significant difference in median value above or below random expert sampling. A p-value <0.05 represents an insignificant difference in median value above or below random expert sampling meaning given the data there is no better or worse performance of random expert sampling to inter-expert or majority vote. To evaluate for ischemic core volume size that alters clinical treatment decisions based on ANGEL-ASPECT and SELECT-2, the predicted segmentations were classified in <1 ml, <50 ml, <100 ml and >100 ml and compared to the median expert volume with Cohen's for random sampling and majority vote and Fleiss' kappa for the inter-expert volumes. For Cohen's kappa the ordinal classes between the median expert volume and predicted of the respective training schemes are compared and for Fleiss' kappa the ordinal classes between the three experts' volumes are compared.

To put the results into perspective, we computed the Spearman correlation coefficient of the ASPECT score and infarct volumes determined by experts, deep learning models, and CT perfusion to the clinical outcomes. We compared the infarct volumes of the random-model and CT perfusion (<30% CBF) to the 24 h-follow-up DWI (final infarct core) with Bland-Altman plots in patients with full reperfusion (TICI >2B). We analyzed differences in correlation coefficients with Fisher's z-test.

Results: Patient Characteristics

We analyzed 233 randomized and non-randomized (screened, but not enrolled) patients in the DEFUSE 3 trial. 121 patients were women (52%) and the median age was 69 (IQR, 59-78) years. The median onset to image time of the 50 patients with witnessed onset was 10 (IQR, 8-12) hours, and 77 patients presented as wake-up strokes. Further patient characteristics are summarized in Table 1. The expert ischemic core volume, ischemic core estimation on CTP (<30% CBF), and penumbra (Tmax≥6 seconds) volume with perfusion imaging were 8 (IQR, 3-26), 11 (IQR, 2-28), and 104 (IQR, 62-157) ml, respectively.

TABLE 1

Patient characteristics

| Categories | Characteristic | Randomized-Train | Non-randomized-Train | Total-Train | Total-Test | p-value |
|---|---|---|---|---|---|---|
| General | Total Number | 146 | 87 | 233 | 33 | |
| | Age | 70 (59-79) | 67 (58-76) | 69 (59-78) | 71 (64-78) | 0.4 |
| | Female % | 52 | 52 | 52 | 54 | |
| Imaging Characteristics | Expert A Vol. [ml] | 9 (4-21) | 22 (6-69) | 12 (5-32) | | |
| | Expert B Vol. [ml]] | 14 (5-27) | 14 (0-60) | 14 (4-37) | | |
| | Expert C Vol. [ml] | 3 (1-7) | 7 (0-43) | 4 (1-12) | | |
| | Expert D Vol. [ml] | | | | 7 (0-31) | |
| | Expert E Vol. [ml] | | | | 2 (0-9) | |
| | Ischemic Core Vol. [ml] (<30% CBF) | 9 (2-27) | 18 (0-77) | 11 (2-38) | | |
| | Tmax6 Vol. [ml][2] | 117 (78-158) | 69 (3-150) | 104 (62-157) | | |
| | ASPECTS on Baseline CT[3] | 8 (7-9) | 8 (5-10) | 8 (7-9) | | |
| Process | Witnessed Number | 50 | | 50 | | |
| | Wake-Up Number | 77 | | 77 | | |
| | Unwitnessed Number | 19 | | 19 | | |
| | Onset to Image Time [h] | 10 (8-12) | | 10 (8-12) | 10 (5-13) | 0.43 |

TABLE 1-continued

Patient characteristics

| Categories | Characteristic | Randomized-Train | Non-randomized-Train | Total-Train | Total-Test | p-value |
|---|---|---|---|---|---|---|
| Follow- | 24 h DWI Number | 146 | | 146 | | |
| Up | 24 h DWI Volume [ml] | 39 | | 39 | | |
| | | (24-110) | | (24-110) | | |
| Clinical | mRS[5] at Baseline | 0 | | 0 | 0 | |
| | | (0-0) | | (0-0) | (0-0) | |
| Outcome | mRS[5] at 90 days | 4 | | 4 | 2 | 0.002 |
| | | (2-5) | | (2-5) | (1-3) | |

Randomized-Train, Non-randomized-Train, Total-Train columns: Median (1st-3rd quantile), if not otherwise indicated; Tmax6 volume: Time-to-Maximum after 6 seconds; ASPECTS on Baseline CT: Alberta Stroke Program Early CT Score; mRS: modified Ranking Scale; p-value column: double sided Wilcoxon test.

TABLE 2

Segmentation Evaluation DEFUSE 3

| Categories | Metric | Random Sampling | inter-expert | p-value random-inter-expert | Majority vote | p-value random-majority |
|---|---|---|---|---|---|---|
| Volume | VS | 0.71 ± 0.04 | 0.55 ± 0.06 | <0.0001 | 0.45 ± 0.09 | <0.0001 |
| | AVD [ml] | 5.36 ± 0.87 | 8.85 ± 1.46 | <0.0001 | 7.91 ± 1.74 | <0.0001 |
| Overlap | Dice | 0.51 ± 0.04 | 0.36 ± 0.05 | <0.0001 | 0.45 ± 0.05 | <0.0001 |
| | Precision | 0.61 ± 0.07 | 0.53 ± 0.03 | <0.05 | 0.79 ± 0.04 | <0.0001 |
| | Recall | 0.60 ± 0.05 | 0.47 ± 0.03 | <0.0001 | 0.38 ± 0.06 | <0.0001 |
| Distance | HD 95 [mm] | 13.60 ± 2.01 | 17.54 ± 2.01 | <0.0001 | 10.92 ± 1.72 | non-sig |
| | SDT 5 mm | 0.71 ± 0.03 | 0.60 ± 0.05 | <0.0001 | 0.75 ± 0.03 | non-sig |

VS = Volumetric Similarity,
AVD = Absolute Volume Difference,
HD 95 = Hausdorff Distance 95th percentile,
SDT = Surface Dice at Tolerance,
Median ± 95% CI (bootstrapped) compared to Expert A, B, C,
p-values of two-sided Wilcoxon sign rank test.

Results: Model Performance

The random expert sampling showed statistically significant superior performance compared to the inter-expert agreement in all metrics. It also outperformed the majority vote training scheme significantly (median #95% CI (bootstrapped) random expert sampling vs. majority vote, Surface Dice at Tolerance 0.71±0.03 vs. 0.60±0.05, 0.68±0.05, Dice 0.50±0.04 vs. 0.31±0.04, Absolute Volume Difference of 5.4±1.3 ml vs. 10.2±2.1 ml, (Table 2).

Figure 2B:
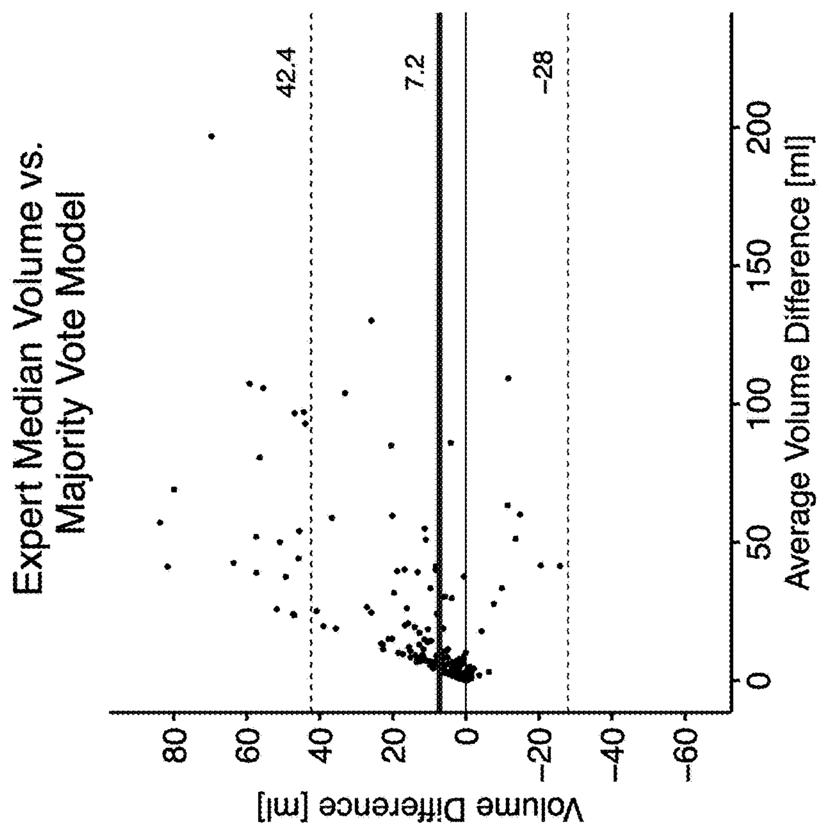
FIGS. 2A-2B are Bland-Altman plots showing Random Expert Sampling (FIG. 2A) and Majority-Model Volume (FIG. 2B) estimates compared to Median Expert Volume.
Figure 2A:
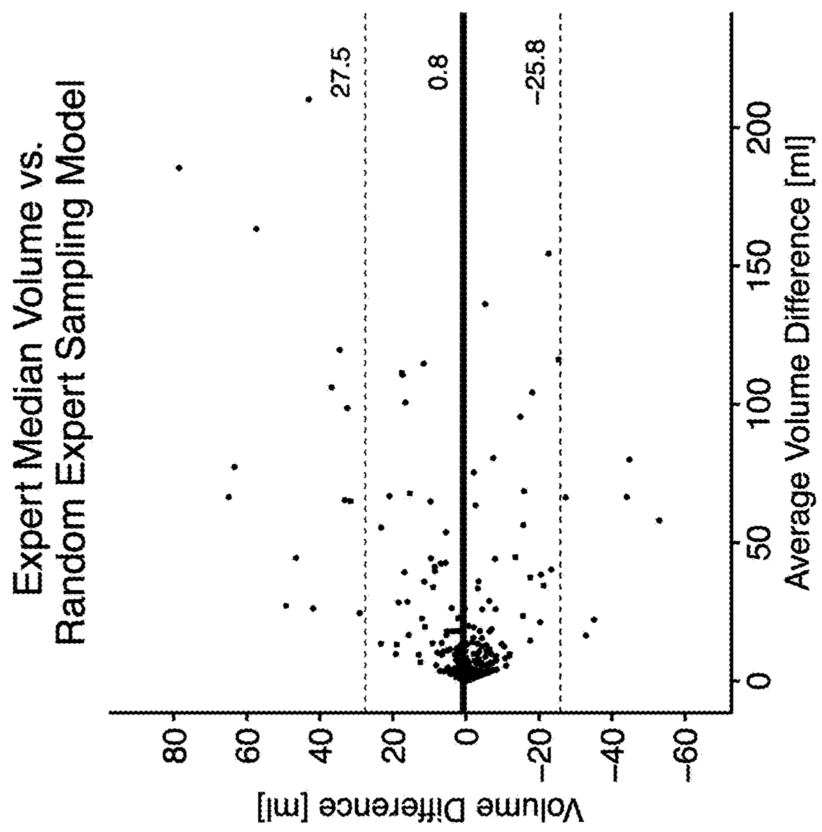

The model-based segmentation with the random expert sampling showed a smaller average volume difference and 95% CI when compared to the median expert volume. The majority vote tended to underestimate the median expert volume. FIGS. 2A-2B are Bland-Altman plots showing Random Expert Sampling (FIG. 2A) and Majority-Model Volume (FIG. 2B) estimates compared to Median Expert Volume.

The findings in the external test set are consistent with those seen in the internal test set, but the test set size is underpowered to confirm the superiority of random experts over the inter-reader segmentation agreement (see Tables 6 and 7).

Figure 4:
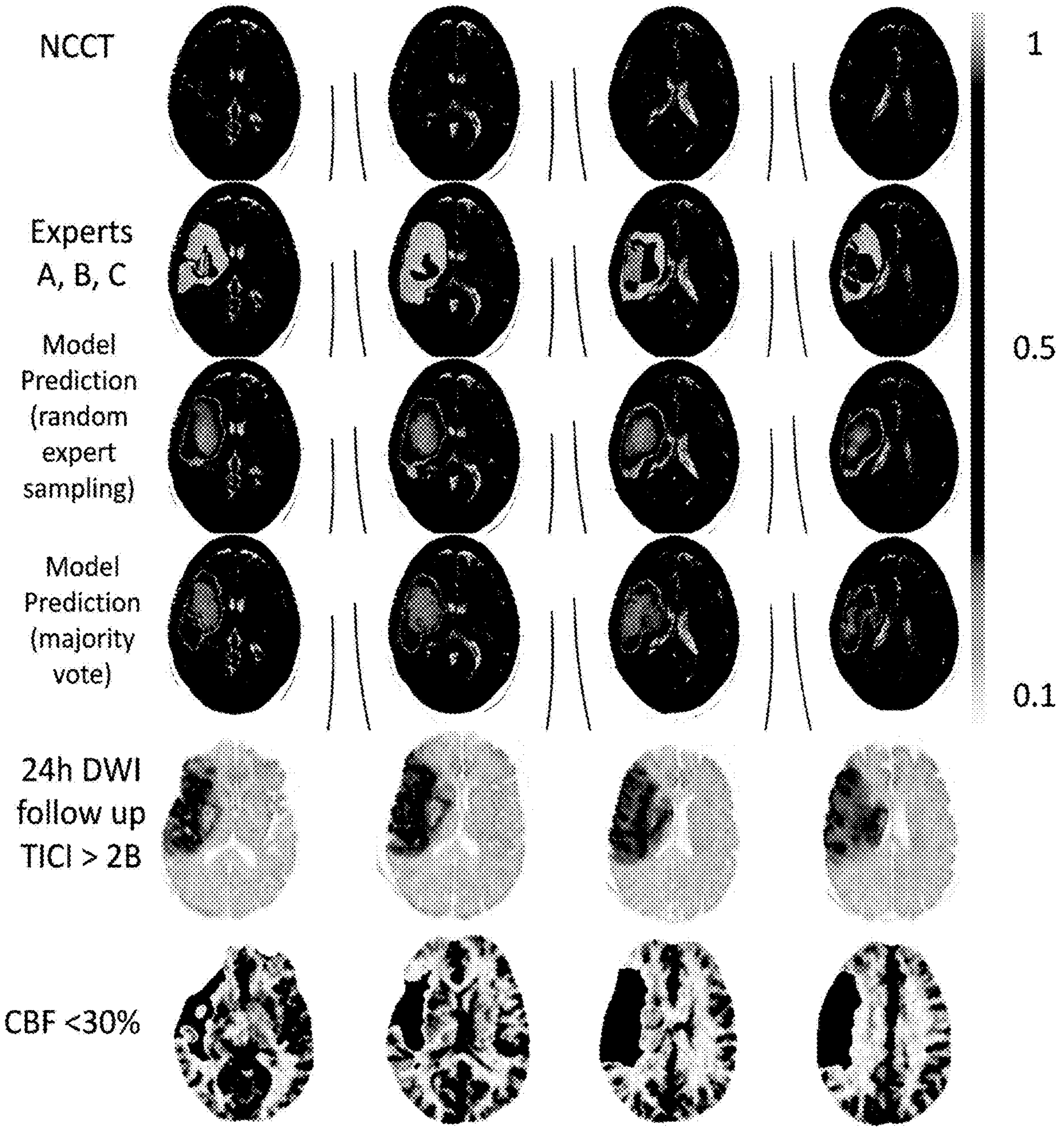
FIG. 4 shows a collection of heatmap images comparing expert segmentation to that of models trained on random expert sampling and majority vote, as well as DWI and perfusion core estimations. Low values are represented by lighter grey, and high values by darker grey. The prediction of a majority vote underestimates acute ischemic brain tissue and may overfit to noise within the lesion.

Qualitatively, the probability predictions of random expert sampling correlate better to the segmentations of the experts than to the predictions for the majority vote which may show overfitting to the singular hypodense voxels and image noise in the outer regions. Random expert sampling prediction covers the lesion area present on DWI, especially within the basal ganglia. FIG. 4 shows a collection of heatmap images comparing expert segmentation to that of models trained on random expert sampling and majority vote, as well as DWI and perfusion core estimations. Low values are represented by lighter grey, and high values by darker grey. The prediction of a majority vote underestimates acute ischemic brain tissue and may overfit to noise within the lesion.

The random-model had similar performance for classifying cases into lesion versus no lesion when compared with the inter-expert agreement and the majority-model, respectively (AUC 0.92±0.02 vs. 0.93±0.02) (Table 3). However, on the external validation set, the classification accuracy was lower compared to the inter-expert agreement (AUC 0.74±0.09 vs. 0.93±0.02).

TABLE 3

Image Classification with 1 ml threshold DEFUSE 3

| Categories | Metric | Random Sampling | inter-expert | Majority Vote |
|---|---|---|---|---|
| Image-level | Dice | 0.85 ± 0.02 | 0.85 ± 0.02 | 0.77 ± 0.02 |
| classification | AUC | 0.92 ± 0.02 | 0.93 ± 0.02 | 0.90 ± 0.03 |
| | Sensitivity | 0.94 ± 0.02 | 0.91 ± 0.02 | 0.65 ± 0.03 |
| | Specificity | 0.70 ± 0.03 | 0.99 ± 0.03 | 0.97 ± 0.01 |

Random Sampling, inter-expert, and Majority Vote columns: Median ± 95% CI (bootstrapped) compared to Expert A, B, C.

Results: Evaluation of NCCT Ischemic Core Volume as Imaging Biomarker in Clinical Practice To determine how the model compared to common ischemic core thresholds, we performed a volume classification analysis using our model. Cohen's kappa for volume classification (<1 ml, <50 ml, <100 ml, and <100 ml) of the random-model is higher than Fleiss' kappa for inter-expert agreement and Cohen's kappa for the majority-model (0.52±10.06 vs. 0.32±0.04 and 0.24±0.05).

When comparing the initial ischemic core volume to the clinical outcome (mRS 90 days), the random experts sampling model volume and ASPECTS correlate significantly to the mRS scores at 90 days, whereas the majority vote and median expert volume do not (Table 4).

TABLE 4

Correlation to the clinical outcome for ASPECTS and volume estimates

| Predictor | Rho of mRS 90 days | p-value |
|---|---|---|
| ASPECT | −0.19 | <0.05 |
| Median expert volume | 0.16 | non-sig |
| Volume of majority-model | 0.15 | non-sig |
| Volume of random-model | 0.19 | <0.05 |

Spearman's Rho and p-value for correlation
Alberta Stroke Program Early CT Score
Computer Tomography Perfusion, Cerebral blood flow (CBF) <30%.

Figure 3A:
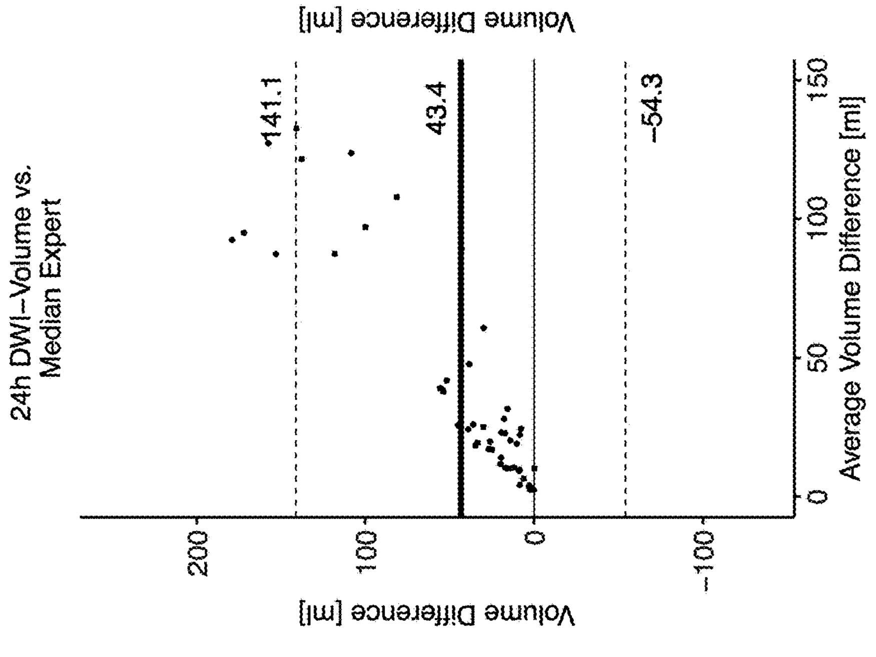
FIGS. 3A-3C are Bland-Altman plots for Median Expert Volume (FIG. 3A), Random Model Volume (FIG. 3B) and CTP Ischemic Core Volume <30% (FIG. 3C) compared to 24 h DWI-Volume for all patient with successful recanalization of the occluded vessel (TICI >2B).
Figure 3B:
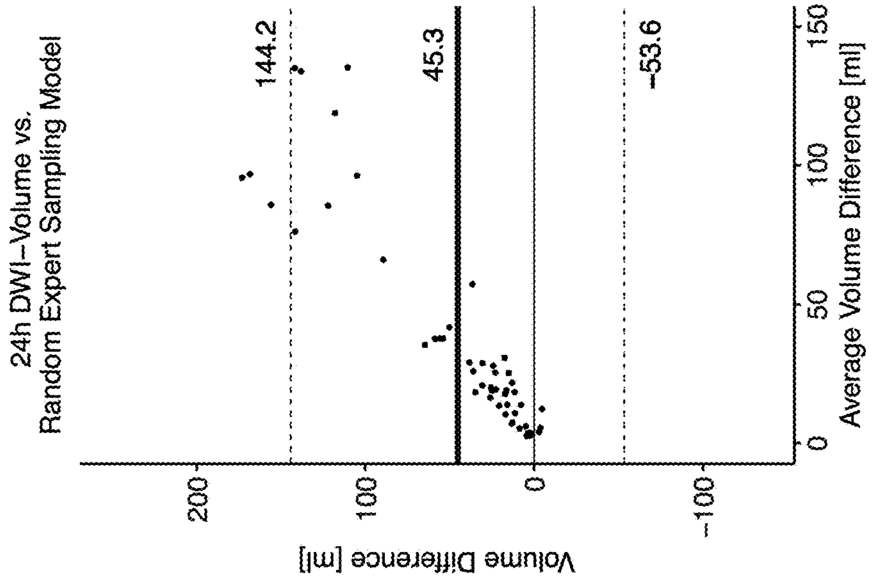
Figure 3C:
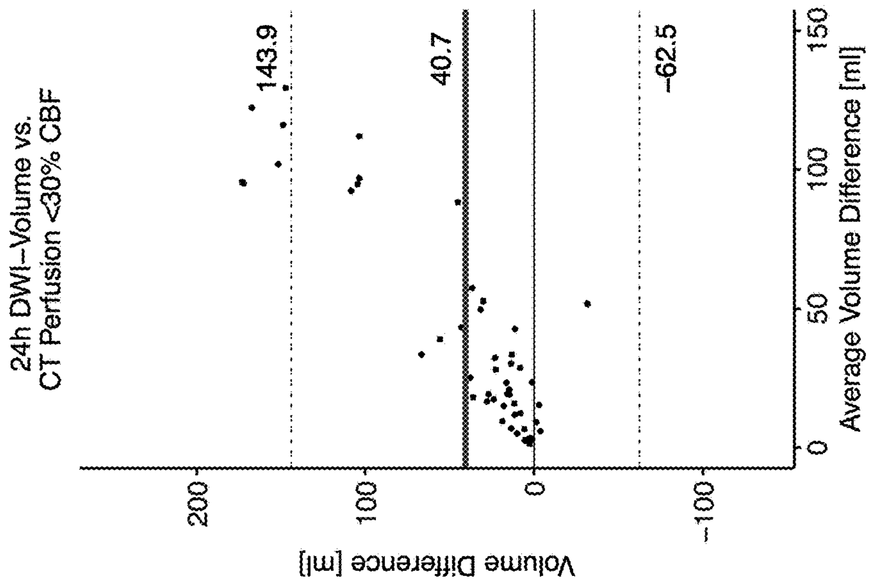
Figure 8A:
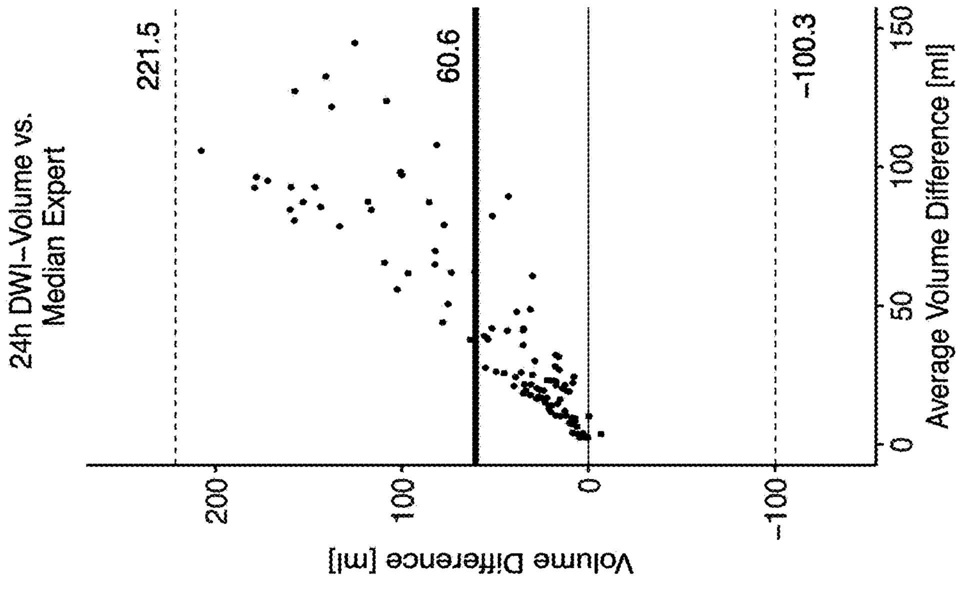
FIGS. 8A-8C are Bland-Altman plots for Median Expert Volume (FIG. 8A), Random Model Volume (FIG. 8B) and CTP Ischemic Core Volume <30% (FIG. 8C) compared to 24 h DWI-Volume for over entire patient population regardless of reperfusion status (all TICI grades).
Figure 8B:
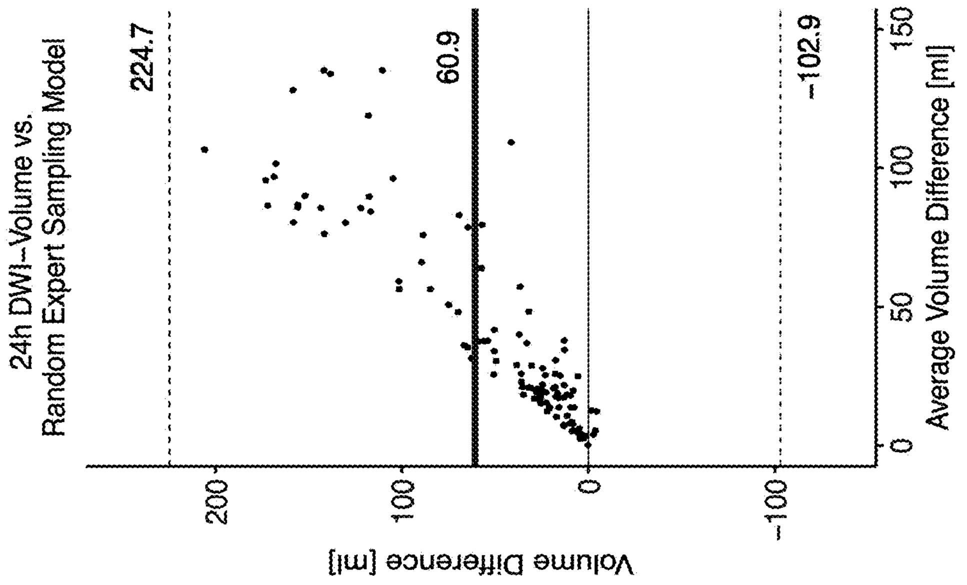
Figure 8C:
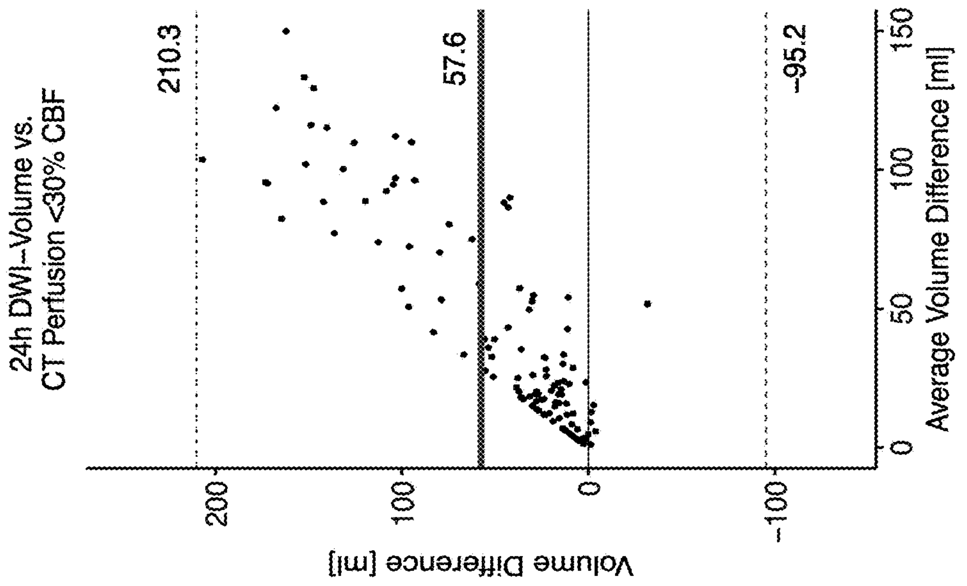
Figure 9A:
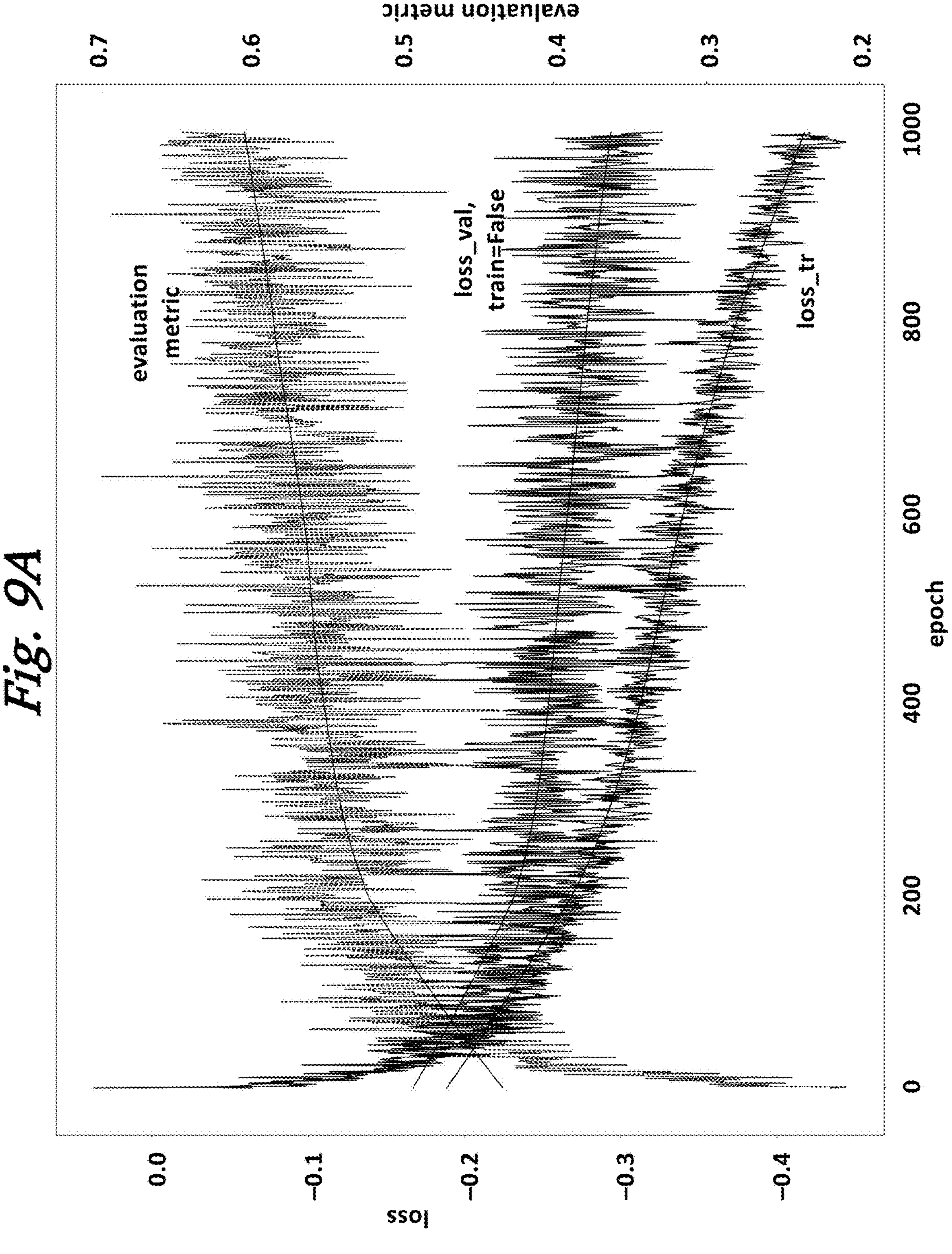
FIG. 9A, FIG. 9B, FIG. 9C, FIG. 9D, FIG. 9E are training loss graphs for random expert sampling (random model) for five folds of training sets. The middle line is the test loss, the bottom line is the training loss, and the top line is the evaluation metric (Dice score). The left y-axis describes the loss, the right y-axis describes the evaluation metric (Dice score) and the x-axis describes the number of epochs. All models converged by epoch 700.
Figure 9B:
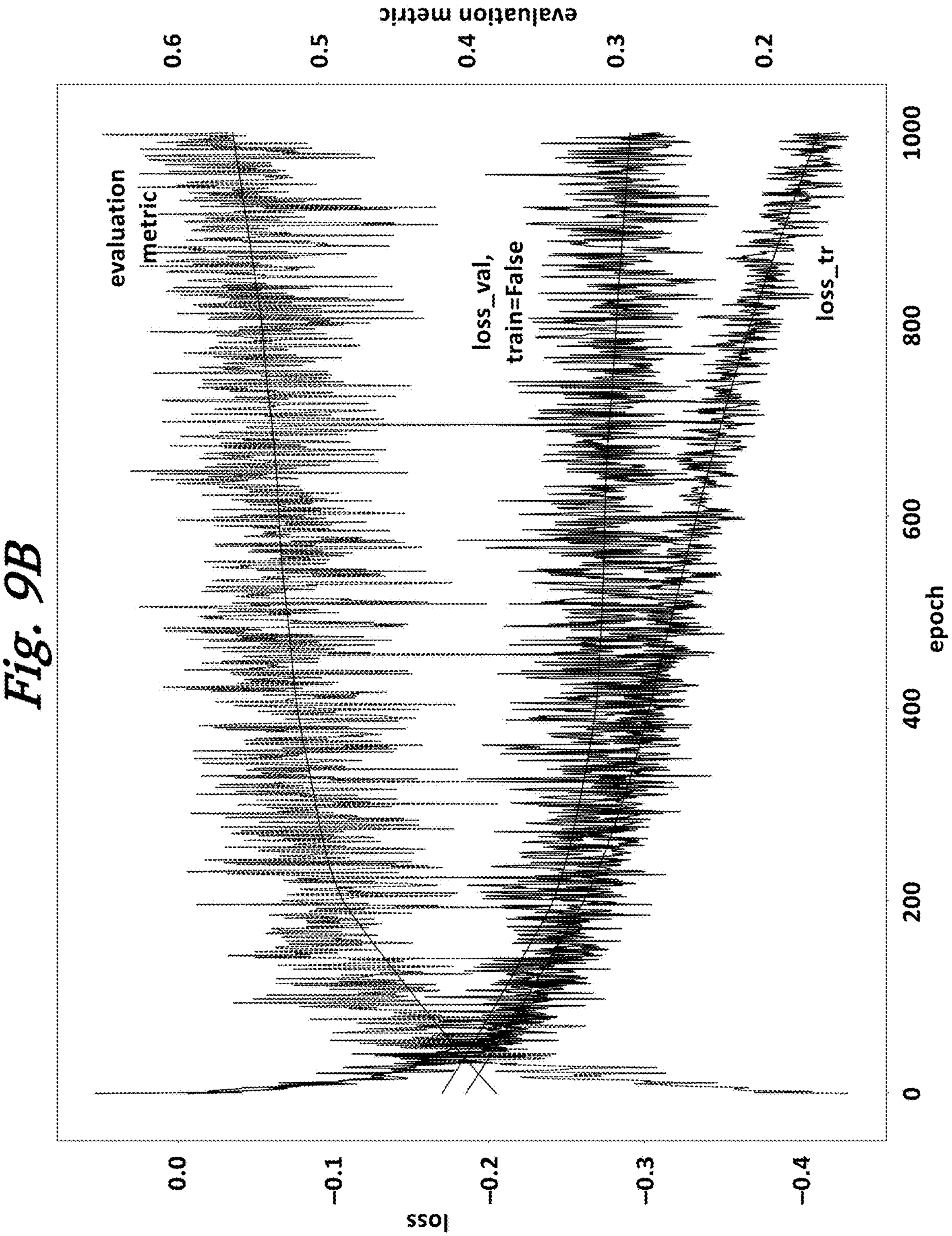
Figure 9C:
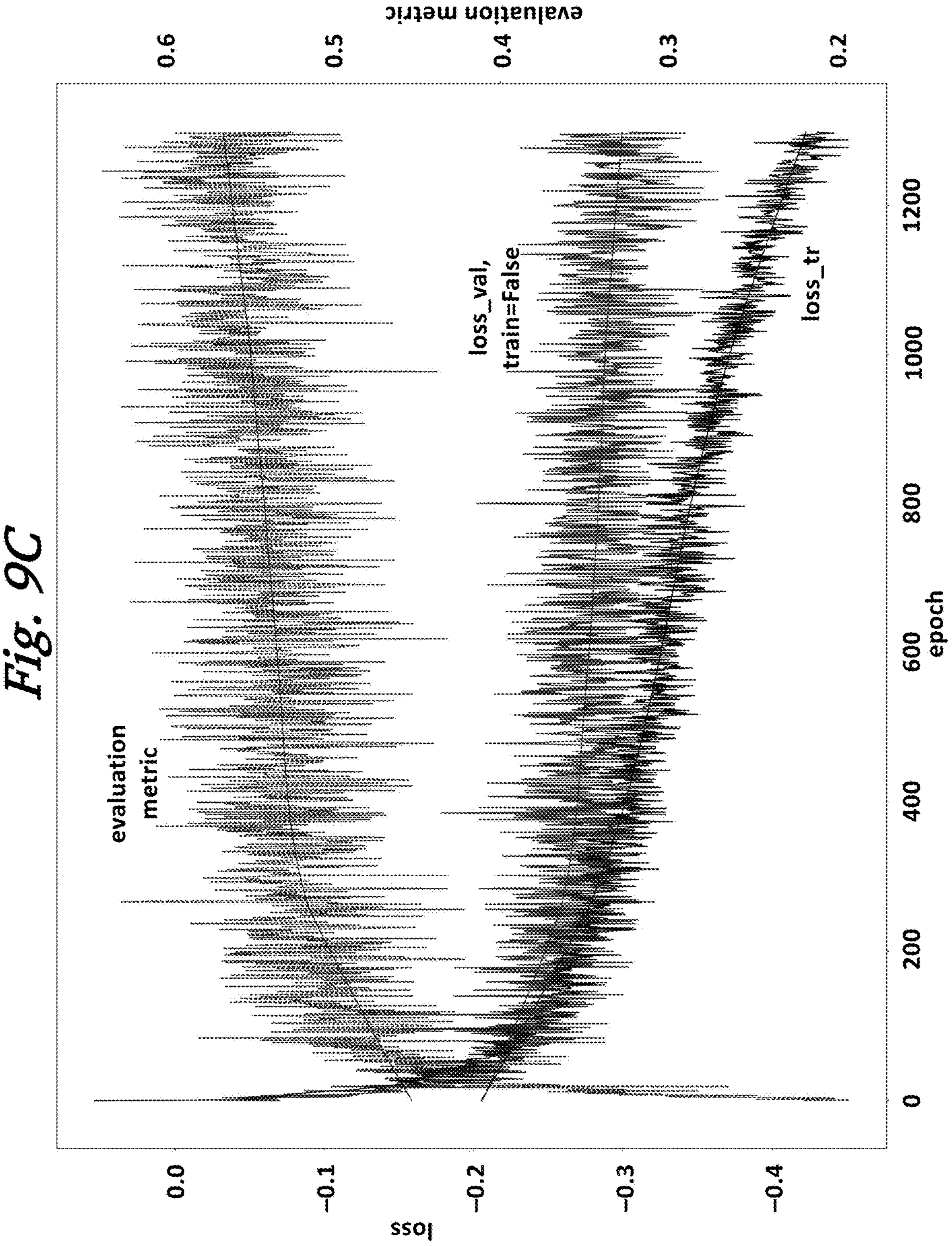
Figure 9D:
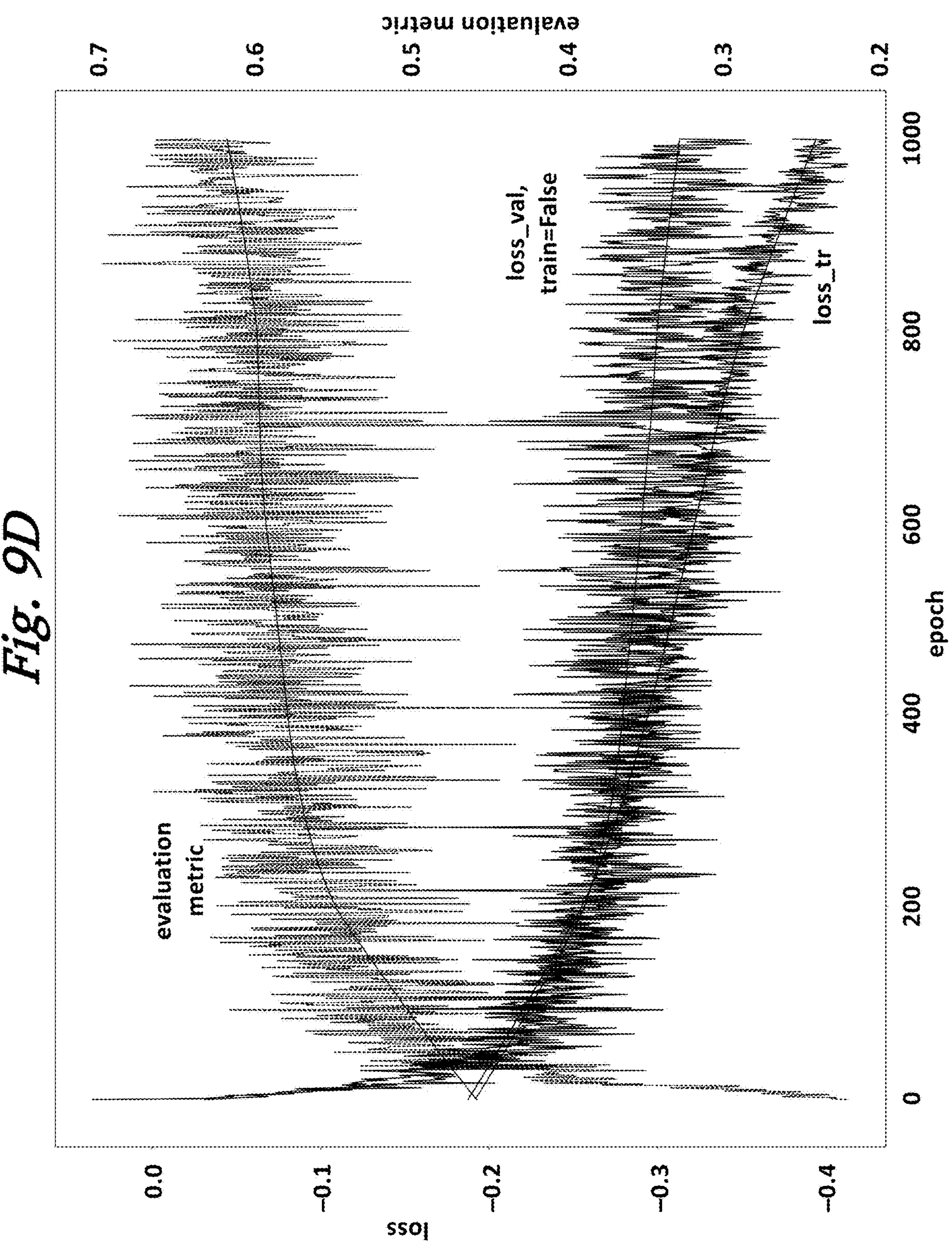
Figure 9E:
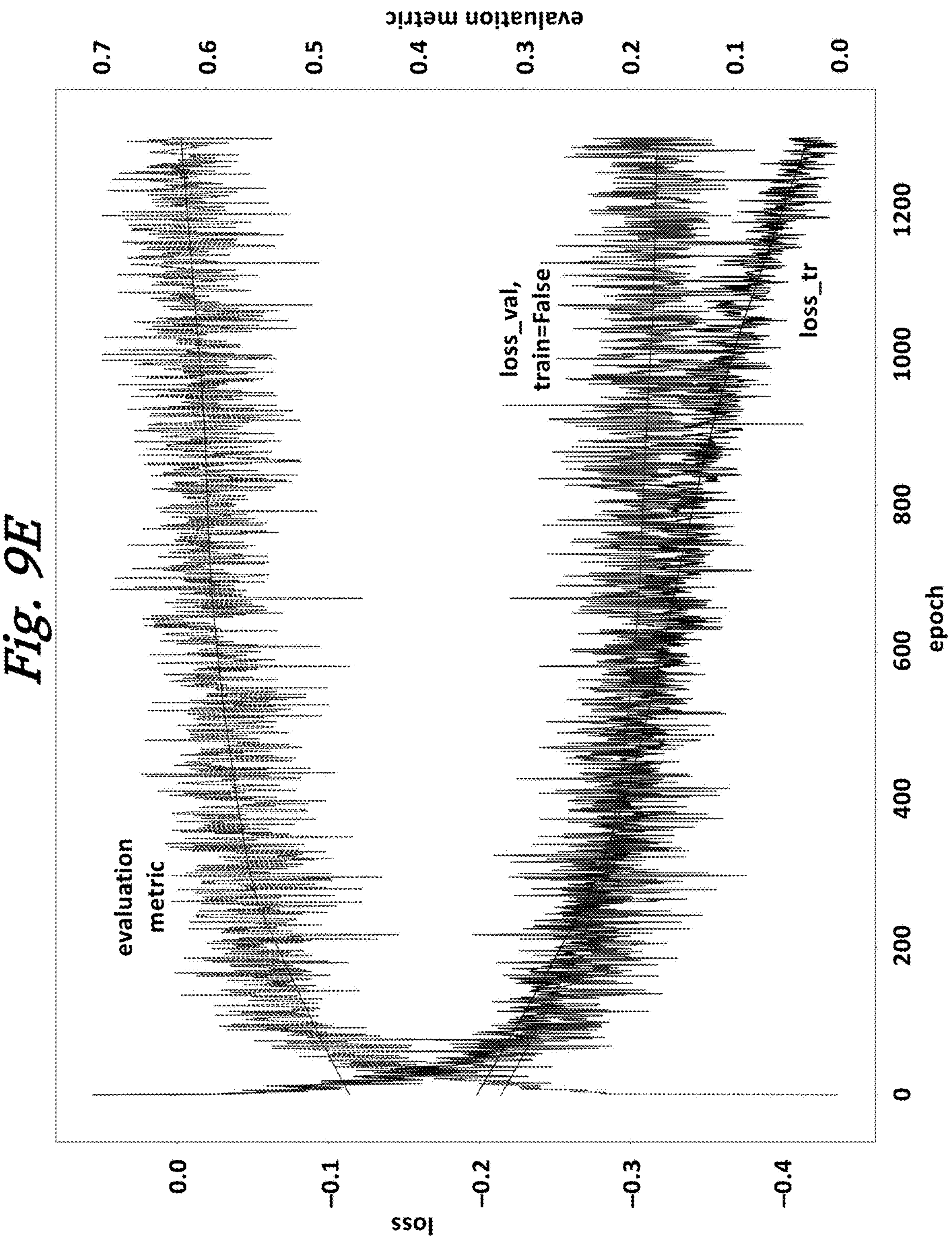

FIGS. 3A-3C are Bland-Altman plots for Median Expert Volume (FIG. 3A), Random Model Volume (FIG. 3B) and CTP Ischemic Core Volume <30% (FIG. 3C) compared to 24 h DWI-Volume for all patient with successful recanalization of the occluded vessel (TICI >2B). FIGS. 8A-8C are Bland-Altman plots for Median Expert Volume (FIG. 8A), Random Model Volume (FIG. 8B) and CTP Ischemic Core Volume <30% (FIG. 8C) compared to 24 h DWI-Volume for over entire patient population (all TICI classes, regardless of successful recanalization). Subgroup analysis of patients with full reperfusion (TICI >2B, n=51) shows no significant difference when comparing the volume correlations to the 24 h-follow-up DWI volume (Spearman rho) of median expert volume, random expert sampling volume prediction and majority vote volume prediction compared to CT perfusion (<30% CBF) volume (Fisher's z-test p-value >0.05, Bland-Altman plot FIGS. 3A-3C and for all patients Bland-Altman plot see FIGS. 8A-8C).

Discussion

In this study, we found that random expert sampling training of a benchmark deep learning model leads to significantly superior agreement with experts than experts among themselves for the segmentation of ischemia on NCCT. We found that compared to prior deep learning applications, fusion techniques such as a majority vote cause the model to overfit to single voxel values and segment less meaningful clinical information. The model-based ischemic core shows similar volume agreement with the final infarct volume and correlation to the clinical outcomes when compared with a CT perfusion core estimation method. Our findings have important implications for future artificial intelligence applications in ischemic stroke imaging.

Multiple trials (ECASS I, ESCAPE, REVASCAT, SWIFT-PRIME, EXTEND-IA, DAWN, DEFUSE 3, ANGEL-ASPECTS, RESCUE Japan-LIMIT, SELECT-2 and TENSION) have included the measures of ischemic injury or the ischemic core on NCCT as inclusion criteria for patients with acute ischemic stroke. Although ASPECTS is widely used to identify ischemic stroke patients who are eligible for endovascular treatment, it is limited by inter-rater variability and has only a modest correlation to ischemic core volumes and location. Our results suggest that a deep learning model can accurately assess volumetric measurements of ischemic injury on non-contrast CT, with its predictions aligning well with advanced imaging techniques and outperforming the agreement between different experts. We hypothesize that use of our model may be helpful to standardize patient treatment decisions and to provide more meaningful information regarding long-term prognosis, although further studies are needed to test these ideas.

What constitutes the ischemic core has become controversial. The ischemic core is best determined by diffusion-weighted imaging (DWI) MRI, but this technique is less commonly used compared to CT-based techniques. The ischemic core on CT is well delineated by CTP-based techniques, but these techniques show imperfect agreement with DWI and are not available at every hospital. New techniques that accurately measure the ischemic core on NCCT are highly desirable given how readily such techniques would be generalizable to most hospitals, and our findings suggest that artificial intelligence models are a promising solution to this need.

The optimal method by which to train artificial intelligence models for the detection and delineation of the ischemic core remains uncertain. Prior studies have used DWI obtained shortly after NCCT as the ground-truth for the ischemic core, but very few institutions have datasets that enable this training approach. Furthermore, the image correlation of the underlying ischemic core pathology of a DWI lesion on NCCT, especially in very early time windows, is uncertain given that hypodensity on NCCT often takes hours to develop, which has limited voxel-wise comparisons of NCCT and DWI. In our study, we sought to circumvent these limitations by using a deep-learning segmentation model. In our model, we used an expert sampling training scheme to improve the performance for ischemic injury delineation on NCCT, and our model performed well for this task. We hypothesize that the broad application of our model may alleviate the limitations of ASPECTS and other imaging techniques that are designed to quantify cerebral ischemia on NCCT.

In segmentation tasks with reference annotation of uncertainty, small target lesions, or empty segmentations, reference annotations require at least highly skilled experts to minimize the errors, and multiple experts' segmentations are needed to approximate the distribution of interpretations, which is resource- and time-intensive.

For acute ischemic stroke segmentation on NCCT, fusion methods for categorical voxel classes may limit the ability of the model to learn segmentation tasks where experts inherently disagree. We found that advanced fusion methods, such as STAPLE or SIMPLE are not applicable due to convergence issues caused by empty labels and higher variability across experts' labels. We tested majority voting and found that it had only modest performance.

In the example discussed here, we only use a patient cohort of one multi-center clinical trial including patients in late time windows (6-16 hours from symptom onset). We found a similar model performance on the international single-center diverse clinical external validation set with only 33 patients included compared to the inter-expert agreement. These are just examples and implementations are not limited by these particular data sets. Recurring local validation may be more informative and feasible than larger and multi-center external test sets. For the image classification, this example did not include stroke mimics or hemorrhagic stroke patients. The method of this invention may be applied in a broader and prospective patient population than these examples.

It is noted that the three neuroimaging experts may not be representative of all readers. The distribution of image interpretation may be improved by additional neuroradiologists' input. The techniques of course are not limited to the use of just three experts.

The performance of this technique may be improved by a careful choice of hyperparameters for a specific patient population or model architecture. This study also aims to compare a multi-rater training methodology for uncertain, small, or empty reference annotations with a standardized deep-learning framework. Other deep learning frameworks and architectures may be used. Lastly, it is noted that the inclusion of patients based on reperfusion status (TICI 2b-3) for mRS correlation analysis may not account for all variables that influence the clinical outcome. However, all images used in this analysis were obtained immediately before thrombectomy, which limits the impact of variables such as transfer time on infarct growth. These specifics of the example image data do not limit the technique in general.

The method is not restricted to randomly sampling different manual ground truth labels of neuroradiologists, but may alternatively use random sampling ground truth labels that are derived from different imaging modalities if in close time proximity to the NCCT. In the embodiments discussed above, the labels come from expert neuroradiologists. However, the essential feature of the present technique the random sampling of labels, and not necessarily the source of the labels. Although in the examples above, the labels come from experts, they could also come from another source. For example, the labels can potentially come from CT or MR perfusion or standard DWI(MRT) based automated algorithms if in close time proximity to the NCCT.

Conclusion

The present invention provides a training approach for multi-expert training that maximizes the encoded information of the NCCT interpretations from expert neuroradiologists. The model trained with this combined encoded information (random expert sampling) performed significantly better than the inter-human-reader agreement. We also have demonstrated that random expert sampling performs better in overlap and volume metrics than the more conventional majority vote. We show numerical better performance than previous works. When comparing the model-based volume and CT Perfusion core volume to the final infarct volume we could find no significant difference in final infarct estimation, which indicates that our model performs similar to advanced CT-based techniques like CTP for delineation of the ischemic core.

Mathematical Derivation: Cross Entropy Loss as Product of Bernoulli Maximum Likelihood Estimation While using majority vote preprocessing of data results in a regression problem, optimizing the cross entropy loss corresponds to a maximum likelihood estimation by recovering the probability distribution that is most likely to have produced the data.

In fact, maximizing the cross entropy loss corresponds to maximizing the likelihood of producing the data when assuming each voxel labeling is independent.

Under that assumption, the log-likelihood of getting a labeling $\{k_i\}$, i indexing voxels can be transformed into the cross entropy loss with the following standard transformation:

$$
\begin{aligned}
\text{log\_likelihood} &= \log\left(\prod_{i|k_i=1} p_i \prod_{i|k_i=0} (1-p_i)\right) \\
&= \log\left(\prod_{i|k_i=1} p_i \prod_{i|k_i=0} (1-p_i)\right) \\
&= \sum_{i|k_i=1} \log(p_i) + \sum_{i|k_i=0} \log(1-p_i) \\
&= \sum_{i|k_i=1} k_i \log(p_i) + \sum_{i|k_i=0} (1-k_i)\log(1-p_i) \\
&= \sum_i k_i \log(p_i) + (1-k_i)\log(1-p_i)
\end{aligned}
$$

TABLE 5

Definitions of Performance Metrics for Medical Image Segmentation

| Category | Metric | Abbreviation | Definition |
|---|---|---|---|
| Volume | Volumetric Similarity | VS | $1 - \frac{\left\|\|\hat{V}\| - \|V\|\right\|}{\|\hat{V}\| + \|V\| + \epsilon}$ |
| | Absolute Volume Difference | AVD | $\frac{1}{m}\sum_{i=1}^{m}\left\|V^i - \hat{V}^i\right\|$ |
| Overlap | Dice Similarity Coefficient | Dice | $\frac{2 \times TP}{2 \times TP + FN + FP}$ |
| | Recall = Sensitivity | Recall | $\frac{TP}{TP + FN}$ |
| | Precision | Precision | $\frac{TP}{TP + FP}$ |
| Distance | Hausdorff Distance, q = 95th percentile | HD 95 | max (h(A, B), h(B, A)) with $h(A, B) = \max_{a \in A} \min_{b \in B} \\|b - a\\|$ |
| | Surface Dice at Tolerance | — | $\frac{\left\|\hat{S} \cap B^t\right\| + \left\|S \cap \hat{B}^t\right\|}{\|\hat{S}\| + \|S\|}$ |

TABLE 5-continued

| Definitions of Performance Metrics for Medical Image Segmentation | | | |
|---|---|---|---|
| Category | Metric | Abbreviation | Definition |
| Image-level classification | Correct Classification Rate | CCR | $\frac{\text{number of correctly detected subjects}}{\text{number of all subjects}}$ |
| | Sensitivity | Sensitivity | $\frac{TP_i}{TP_i + FN_i}$ |
| | Specificity | Specificity | $\frac{TN_i}{TN_i + FP_i}$ |
| | Area Under the Curve | AUC | |

V = ground truth volume,
$\hat{V}$ = predicted volume,
TP = True Positive voxels,
TN = True Negative voxels,
FP = False Positive voxels,
FN = False Negative voxels,
S = surface voxels of ground truth,
$\hat{S}$ = predicted surface voxels,
$B^t$ = border volume of ground truth defined by tolerance t,
$\hat{B}^t$ = predicted border volume defined by tolerance t.

TABLE 6

| Segmentation, External Evaluation | | | | | | |
|---|---|---|---|---|---|---|
| Categories | Metric | Random Sampling | inter-expert | p-value random-inter-expert | Majority Vote | p-value random-majority |
| Volume | VS | 0.36 ± 0.21 | 0.78 ± 0.28 | non-sig | 0.32 ± 0.49 | non-sig |
| | AVD [ml] | 5.40 ± 4.02 | 7.53 ± 10.5 | non-sig | 10.10 ± 11.67 | <0.0001 |
| Overlap | Dice | 0.42 ± 0.13 | 0.44 ± 0.2 | non-sig | 0.24 ± 0.1 | non-sig |
| | Precision | 0.34 ± 0.13 | 0.30 ± 0.19 | non-sig | 0.15 ± 0.08 | non-sig |
| | Recall | 0.75 ± 0.18 | 0.76 ± 0.27 | non-sig | 0.90 ± 0.09 | non-sig |
| Distance | HD 95 [mm] | 18.95 ± 12.33 | 35.00 ± 15.31 | non-sig | 23.44 ± 5.1 | non-sig |
| | SDT 5 mm | 0.64 ± 0.13 | 0.58 ± 0.24 | non-sig | 0.49 ± 0.11 | non-sig |

VS = Volumetric Similarity,
AVD = Absolute Volume Difference,
HD 95 = Hausdorff Distance 95th percentile,
SDT = Surface Dice at Tolerance,
Random Sampling, inter-expert, and Majority Vote columns: Median ± 95% CI (bootstrapped) compared to Expert D and Expert E
p-value columns: p-values of two-sided Wilcoxon sign rank test.

TABLE 7

| Image Classification with 1 ml threshold, External Evaluation | | | | |
|---|---|---|---|---|
| Categories | Metric | Random Sampling | inter-expert | Majority Vote |
| Image-level Classification | Dice | 0.75 ± 0.06 | 0.77 ± 0.07 | 0.58 ± 0.11 |
| | AUC | 0.72 | 0.80 | 0.90 |
| | Sensitivity | 0.65 ± 0.08 | 0.71 ± 0.1 | 0.69 ± 0.05 |
| | Specificity | 0.67 ± 0.1 | 0.75 ± 0.13 | 0.80 ± 0.05 |

Random Sampling, inter-expert, and Majority Vote columns: Median ± 95% CI (bootstrapped) compared to Expert D and E.

The invention claimed is:

1. A method for generating segmentation masks to assist in identification of acute ischemic stroke, the method comprising:

(a) performing a non-contrast computed tomography scan to produce a computed tomography image;

(b) inputting the computed tomography image to an input layer of a deep learning neural network;

(c) outputting a segmentation mask of acute ischemic stroke from an output layer of the deep learning neural network, wherein the segmentation mask of acute ischemic stroke is generated in response to the computed tomography image input to the deep learning neural network;

wherein the deep learning neural network is trained with a training set comprising ground truth non-contrast computed tomography images and corresponding segmentation masks of acute ischemic stroke, wherein the training set comprises multiple segmentation masks of acute ischemic stroke for each of the non-contrast computed tomography images; and wherein one of the multiple segmentation masks is randomly and uniformly sampled from the multiple segmentation masks for training.

2. The method of claim 1 wherein the corresponding segmentation masks of acute ischemic stroke are manually generated by neuroradiologists.

3. The method of claim 1 wherein the corresponding segmentation masks of acute ischemic stroke are generated using automated CT or MR perfusion.

4. The method of claim 1 wherein the corresponding segmentation masks of acute ischemic stroke are generated using standard DWI (MRT).

5. The method of claim 1 wherein the deep learning neural network has a nnUNet architecture with multiple stages with two 3D convolutions per stage, and leaky ReLU as activation function.

* * * * *